(12) United States Patent
Junior et al.

(10) Patent No.: US 8,568,788 B2
(45) Date of Patent: Oct. 29, 2013

(54) NANOPARTICULATED ANESTHETIC COMPOSITION FOR TOPIC USE

(75) Inventors: Dante Alário Junior, São Paulo (BR);
Silvia Stanisçuski Guterres, Porto Alegre (BR); Adriana Raffin Pohlmann, Porto Alegre (BR); Lali Rosoni Zancan, Porto Alegre (BR)

(73) Assignees: Biolab Sanus Farmaceutica Ltda, Sao Paulo (BR); Universidade Federal Do Rio Grande Do Sul, Porto Alegre (BR)

( * ) Notice: Subject to any disclaimer, the term of this patent is extended or adjusted under 35 U.S.C. 154(b) by 607 days.

(21) Appl. No.: 12/531,404

(22) PCT Filed: Mar. 12, 2008

(86) PCT No.: PCT/BR2008/000070
§ 371 (c)(1),
(2), (4) Date: Sep. 15, 2009

(87) PCT Pub. No.: WO2008/113144
PCT Pub. Date: Sep. 25, 2008

(65) Prior Publication Data
US 2010/0086614 A1 Apr. 8, 2010

(30) Foreign Application Priority Data
Mar. 16, 2007 (BR) .................................. 0700832

(51) Int. Cl.
*A61K 9/50* (2006.01)
*A61K 31/16* (2006.01)
(52) U.S. Cl.
USPC ............................ 424/501; 977/773; 514/626
(58) Field of Classification Search
USPC ............................ 424/501; 977/773; 514/626
See application file for complete search history.

(56) References Cited

U.S. PATENT DOCUMENTS

| 4,562,060 A | * | 12/1985 | Broberg et al. | ............... 424/443 |
| 5,993,836 A | * | 11/1999 | Castillo | ....................... 424/401 |
| 2006/0188583 A1 | * | 8/2006 | Lim et al. | ..................... 424/490 |
| 2007/0154527 A1 | * | 7/2007 | Myers et al. | .................. 424/443 |

FOREIGN PATENT DOCUMENTS

| WO | WO 99/01114 A1 | 1/1999 |
| WO | WO 9901114 A1 * | 1/1999 |
| WO | WO 2006/002365 A2 | 1/2006 |
| WO | WO 2006002365 A2 * | 1/2006 |

OTHER PUBLICATIONS

Written Opinion of the International Searching Authority (ISA) (WIPO, Sep. 16, 2009) ([Retrieved from internet <URL: http://www.wipo.int/patentscope/search/en/detail.jsf?docId=WO2008113144&recNum=1&tab=PCTDocuments&maxRec=1&office=&prevFilter=&sortOption=&queryString=FP%3A%28PCT%2FBR2008%2F000070%29 >]), 4 pages.*
Austria-Codex (Emla 5 % Creme (2004/2005), pp. 2038-2041; cited on ISR), 7 pages.*

(Continued)

*Primary Examiner* — Jason M Sims
*Assistant Examiner* — Miriam A Levin
(74) *Attorney, Agent, or Firm* — Arent Fox LLP

(57) ABSTRACT

The present invention relates to a nanoparticulated anaesthetic composition for topical use in which at least one local anaesthetic agent is encapsulated in polymeric nanoparticles. The present invention also relates to the use of such polymeric nanoparticles comprising at least one local anaesthetic agent in the preparation of an anaesthetic composition for topical application to the skin or mucosa.

4 Claims, 2 Drawing Sheets

(56) References Cited

OTHER PUBLICATIONS

Institute of Nanotechnology, Nanocapsules and Dendrimers—Properties and Future Applications, Azonano.com, bottom of p. 1 [Downloaded Dec. 9, 2012] [Retrieved from internet <URL: http://www.azonano.com/article.aspx?ArticleID=1649 >], 2 pages.*

Quenelle et al., Efficacy of Microencapsulated Rifampin in Mycobacterium tuberculosis-infected Mice, Antimicrobial Agents and Chemotherapy (May 1999) 43(5):1144-1151 [Downloaded Dec. 9, 2012] [Retrieved from internet URL: http://aac.asm.org/content/43/5/1144.full.pdf+html >], 9 pages.*

Banai et al., Locally delivered nanoencapsulated tyrphostin (AGL-2043) reduces neointima formation in balloon-injured rat carotid and stented porcine coronary arteries, Biomaterials (2005) 26: 451-461, 11 pages.*

Marchal-Heussler et al., Colloidal drug delivery systems for the eye. A comparison of the efficacy of three different polymers: poly(isobutyl cyanoacrylate), poly(lactic-co-glycolic acid), poly($\epsilon$-caprolactone), S.T.P. Pharma Sciences (1992) 2 (1): 98-104 (Abs. only), 1 page.*

Austria-Codex 2004/2005; Band 59/1; Osterreichische Apotheker-Verlagsgesellschaft m.b.H.; ISBN 3-8520-0163-3, pp. 2038-2041.

\* cited by examiner

NANOPARTICULATED ANESTHETIC COMPOSITION FOR TOPIC USE

CROSS-REFERENCE TO RELATED APPLICATION

This application is a National Stage entry of International Application No. PCT/BR2008/000070, filed Mar. 12, 2008, which claims priority to Brazilian Application No. PI0700832-5, filed Mar. 16, 2007. the disclosure of the prior applications is hereby incorporated in their entirety by reference.

FIELD OF THE INVENTION

The present invention relates to an anaesthetic composition comprising at least one local anaesthetic agent in polymeric nanoparticles, and the use of such polymeric nanoparticles comprising at least one local anaesthetic agent in the preparation of an anaesthetic composition for topical application to the skin or mucosa.

BACKGROUND OF THE INVENTION

Local anaesthetics are drugs that provoke a reduction in sensibility and/or motor functions, in the area of application to the body, by the blocking of nerve conduction. Ideally, a local anaesthetic should neither provoke irritation nor damage to nerve tissue or other tissues close to the area of application. Complementarily, it is desirable that its action remains limited to the area of application, so as to avoid anesthetising other areas and undesirable systemic effects. Furthermore, it is desirable that the analgesic action is prolonged in order to confer an activity exceeding the duration of the pain stimulus (e.g. the time of the surgical intervention).

With the intent of increasing the power and time of activity, as well as reducing the potential adverse effects, various approaches have been attempted to produce local anaesthetics. These include: the combined use of vasoconstrictor agents (e.g. epinephrine), the development of anaesthetic molecules having increased affinity for nerve tissues (e.g. bupivacaine, ropivacaine), the use of formulations in the form of liposomes (e.g. liposomal lidocaine—Elamax®). However, these approaches have the disadvantages of local collateral effects (e.g. tissue necrosis due to prolonged vasoconstriction) or systemic collateral effects (e.g. the risk of cardiac arrhythmia and other cardiovascular problems).

Another approach that has been used is the production of formulations of prolonged-release micro-particles with sizes of over 1 micrometer, based on the use of biodegradable polymers, such as those presented in the publications WO 95/09613, WO 97/49391, EP 1 132 080, WO 02/58670, WO 06/013309, WO 06/047279 and in a series of scientific articles.

However, the large majority of these local anaesthetic formulations have the disadvantage of requiring injection in order to achieve optimal efficiency.

It is worth pointing out that, in the case of injectable formulations, apart from the need to use sterile formulations and administration devices, the process of injecting anaesthetics is painful and causes discomfort, especially in the case of children or in patients with an aversion to injections.

In this context, the topical application of anaesthetics to the skin is an interesting alternative for administering local anaesthetics. However, their application is limited by the low permeability of the skin and by the limited activity time of these formulations.

The low permeability of the skin is due, amongst other factors, to the barrier created by the corneal layer which is formed of corneocytes, having a lipid bilayer that increases resistance to ionised or low liposoluble substances. Thus, the flow through the skin depends on the chemical characteristics of the substances. As a rule, lipid drugs are absorbed through the cornea layer, with variable permeation coefficients, and hydrophilic drugs are almost exclusively absorbed by the paracellular route, with almost constant permeation coefficients. Due to the difficulty of controlling skin penetration by the drugs, chemical and physical agents, as well as carrier systems are presently being studied to overcome such shortcomings. With reference anaesthetic products for topical use on the skin, such as, for example, EMLA® cream (a cream containing 2.5% lidocaine and 2.5% prilocaine, by AstraZeneca do Brasil Ltda.), quite apart from offering inferior anaesthetic efficiency compared to injectable anaesthetics, require times of 1 to 2 hours to produce satisfactory anaesthesia on healthy skin, depending on the type of procedure, with the time of initial activity varying according to the distinct areas of the body (skin or mucosa) and the different skin conditions (with lesions, healthy or thick).

Therefore, the products used as local anaesthetics known and marketed in the actual state-of-the-art present inconveniences. In the case of injectable products, these are related to the manner of administration since the injection process is painful and causes discomfort. On the other hand, in the case of products for topical application to the skin, the disadvantages are related to the low absorption through the skin, length of time to take action and inferior anaesthetic efficiency.

Therefore, intending to obtain local anaesthetic products with appropriate safety and efficiency profiles, administration not requiring injection and reduced time of initial activity, the present invention is the result of research concerning the efficiency of anaesthetic formulations in which the local anaesthetic agent is contained in polymeric nanoparticles, when these are applied topically.

Despite the existence of accounts relating the production of anaesthetic agent nanoparticles in the scientific literature (e.g. Gorner T. e col. "Lidocaine-loaded biodegradable nanospheres I. Optimization of the drug incorporation into the polymer matrix". *Journal of Controlled Release* 57 (1999) 259-268; Polakovic M. e col. "Lidocaine loaded biodegradable nanospheres II. Modelling of drug release". *Journal of Controlled Release* 60 (1999) 169-177; Chung, T. e col. "Effects of solvent evaporation rate on the properties of protein-loaded PLLA and PDLLA microspheres fabricated by emulsion-solvent evaporation process". *J Microencapsul.* 19 (2002) 463-71); Schwarz C & Mehnert W; "Freeze-drying of drug-free and drug-loaded solid lipid nanoparticles (SLN)". *INT. J. PHARM* (1997), V157, P171-9.; Govender T e col.; "Defining the drug incorporation properties of PLA-PEG nanoparticles". *INT. J. PHARM* (2000), V199, p95-110; and in patent documents (e.g. WO 06/056064 that describes a nanoparticulate formulation for injectable administration, mainly intravenously), to the best knowledge of the present inventors, there does not exist any reference in the actual state-of-the-art relating to the efficiency of a local anaesthetic product for topical application to the skin or mucosa comprising an anaesthetic agent in polymeric nanoparticles or any reference to the fact that such a formulation may present superior efficiency to non-nanoparticulate anaesthetic formulations for topical use. In the same context, there is no reference to the surprising fact confirmed by the present inventors that the formulation of anaesthetic agents in polymeric nanoparticles may lead to increased anaesthesia time and better definition of the anaesthetic effect compared to non-nanoparticulate formulations.

In this context, it should be stressed that U.S. Pat. No. 6,203,802 describes methods for the treatment of the superficial layers of the epidermis based on topical application, to the skin, of polymeric nanoparticles encapsulating at least one active ingredient but, however, does not make any reference whatsoever to polymeric nanoparticles for carrying local anaesthetic agents nor any reference whatsoever to the use of such a formulation to cause local anaesthesia, with activity occurring in the derm.

DESCRIPTION OF THE INVENTION

Figure 1:
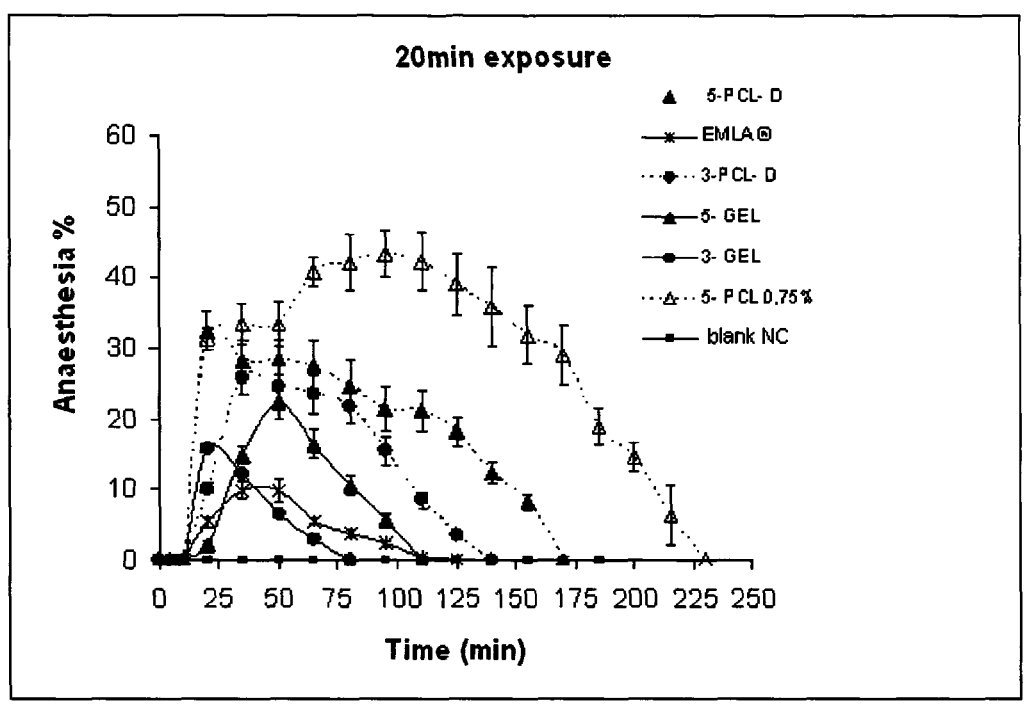
FIG. 1: percentage of anaesthesia promoted by the hydrogels G5-PCL-TWE, G5-EUD-EPK, G3-PCL-TWE, G5-PCL-TWE 0.75% and the commercially available EMLA® cream 20 minutes after topical administration to the tails of rats (n=11/group).

The present invention relates to an anaesthetic composition comprising at least one local anaesthetic agent in polymeric nanoparticles in a therapeutically efficient amount and at least one viscosity increasing agent.

The present invention also relates to the use of such polymeric nanoparticles comprising at least one local anaesthetic agent in the preparation of a local anaesthetic product for topical application to the skin or mucosa/mucous membranes.

In accordance with the present invention, the term polymeric nanoparticles refers to a carrier system for drugs having sizes under 1 µm and in which the active ingredient is retained, encapsulated or adsorbed. The term polymeric nanoparticles may be used to denote nanospheres and nanocapsules. Nanospheres are constituted of a polymer matrix in which the active ingredient is retained, encapsulated or adsorbed. Nanocapsules are constituted of a polymer container enclosing a nucleus, in which the active ingredient may be dissolved, retained, or dispersed in the nucleus and/or adsorbed in the polymeric wall.

Overall, the production processes for polymer nanoparticles may be classified among the methods of in situ polymerisation or methods using pre-formed polymers.

Polymers commonly used in the preparation of nanoparticles are, for example poly (lactide), poly (lactide-glycolide), poly (glycolide), poly (caprolactone), poly (amides), poly (anhydrides), poly (amino acids), poly (esters), poly (cyanoacrylates), poly (phosphazines), poly (phosphoesters), poly (esteramides), poly (dioxanones), poly (acetals), poly (cetals), poly (carbonates), poly (orthocarbonates), degradable poly (urethanes), chitins, chitosans, poly (hydroxybutyrates), poly (hydroxyvalerates), poly (maleic acid), poly (alkylene oxalates), poly (alkylene succinates), poly (hydroxybutyrates-co-hydroxyvalerates), and copolymers, terpolymers, oxidised cellulose, or combinations or mixtures of these materials.

Some polymers that prove to be especially interesting are poly (ε-caprolactone) (PCL; for example, poly (ε-caprolactone) 65 Kd—Sigma Aldrich); methacryllate acid copolymers and methacryllate or acrylic esters (e.g. Eudragits®); poly (alkyl methacrylate); poly (methyl methacryllate) (e.g. PMM).

Polymer nanoparticles may be produced, for example, by the methods (i) of in situ polymerisation of monomers (latex) or dispersion of pre-formed polymers (pseudolatex or artificial latex) as described in De Jaeghere F et al. Nanoparticles. In: Mathiowitz E, ed. *The Encyclopedia of Controlled Drug Delivery*. New York, N.Y.: Wiley and Sons Inc; 1999: 641-664 and Couvreur P, et al. Controlled drug delivery with nanoparticles: *Eur J Pharm Biopharm*. 1995; 41: 2-13; (ii) method of emulsion-evaporation for pharmaceutical use first proposed by Gurny R, Peppas N A, Harrington D D, Banker G S. Development of biodegradable and injectable lattices for controlled release of potent drugs. *Drug Dev Ind Pharm*. 1981; 7: 1-25 based on U.S. Pat. No. 4,177,177, with the polymer being dissolved in a volatile organic solvent immiscible in water. The organic solution is dispersed in an aqueous phase containing emulsifier and oil/water emulsion forming facilitators; and (iii) method of the interface deposit of pre-formed polymers (nanoprecipitation) as described by Fessi et al. in U.S. Pat. No. 5,049,322, with the latter being a particularly interesting process.

The organic solvents that may be used for the preparation of nanoparticles are: small chain alcohols (methanol, ethanol, isopropanol, etc.), small chain ketones (acetone, methyl-ethyl-ketone, etc.), light hydrocarbons or a mixture of light hydrocarbons (hexane, petroleum ether, etc.), lightly chlorated hydrocarbons (chloroform, methylene hydrochloride, tri-hydrochlorideethylene, etc.), or other common light solvents such as acetonitryl, dioxane, etc. Acetone is a particularly interesting solvent.

Surfactants are commonly used to avoid the aggregation of the particles when stored. Examples of surfactants that may be used are: lecithins, synthetic, anionic (e.g. sodium lauryl sulphate), cationic (e.g. quaternary ammonium) or non-ionic (e.g. sorbitan monoesters, containing or not polyoxyethylene residues, ethers formed from fatty alcohols and polyethylene glycol, polyoxyethylene-polypropylene glycol, etc.). Particularly interesting combinations include lipophilic surfactants with low hydrophilic-lipophilic (EHL) balance values (e.g. sorbitan esters—Span® 20 (sorbitan monolaurate) or Span® 60 sorbitan monostearate) and hydrophilic surfactants with high EHL values (ethoxylated sorbitan esters—TWEEN® 80 (polysorbate 80)) or, indeed, merely a single non-ionic surfactant having a high EHL (such as TWEEN® 80 (polysorbate 80)).

In accordance with the present invention, the term local anaesthetic agent refers to drugs that reversibly block nerve conduction when applied to a limited region of the body. The local anaesthetic agents of the present invention may be selected from the group consisting of, but not limited to, benzoate ester or amino-ester, amino-amide anilide, amino-ester naphtoate, benzoic acid, pramoxine, dyclonine, or mexyletine, amongst others; free base anaesthetics: lidocaine, prilocaine, bupivacaine, mepivocaine, ethydrocaine, butanylcaine, trimecaine, or, alternatively, tetracaine, benzocaine, ropivacaine, dibucaine, procaine, chlorprocaine, butambene, picrate, dibucaine, articaine and xylocalne, and their salts, derivates or mixtures. The local anaesthetic may be used in the form of a salt, such as, for example, hydrochloride, hydrobromide, acetate, citrate, carbonate or sulphate.

In accordance with the present invention, the above nanoparticles encapsulating at least one local anaesthetic agent may achieve an equivalent or superior anaesthetic effect using a smaller amount of the local anaesthetic agent, as well as achieving this effect with a more predictable anaesthetic power and longer duration compared to the equivalent non-particulate compositions commercially available such as, for example, EMLA®.

In accordance with one aspect of the present invention, the concentration of at least one of the anaesthetics shall compose approximately 0.5 to 10% of the composition. More specifically, the present invention comprises a combination of at least two anaesthetic agents, such as a combination of lidocaine and prilocaine in a quantity composing approximately 5% of the anaesthetics, with approximately 2.5% of lidocaine and approximately 2.5% of prilocaine.

According to the present invention, the term viscosity enhancer refers to a substance capable of increasing the viscosity of liquid or semi-liquid formulations (e.g. solutions, suspensions, emulsions, creams, ointments gels). The viscosity enhancer agents may be selected from the group consisting of, but not limited to, natural polymers (e.g. cellulose, gums, amides, etc.) or non-natural polymers (e.g. carboxypolymethylene (arbopol), hydroxyethylcellulose, methyl and propyl cellulose, poly(ethyleneglycol), poly(vinylpyrrolidones) (PVP) resins, etc.).

According to a preferential aspect of the invention, the compositions comprising the present invention possess sufficient viscosity to facilitate local application, without flowing or running to unintended areas. More specifically, the compositions comprising the present invention possess a viscosity of over 50 cP and preferentially, over 100 cP. Formulations with a viscosity of approximately 100000 to 800000 cP prove to be interesting because they present good spread control for topical application. Among these, formulations with a viscosity under approximately 650000 cP prove to be even more interesting when compared to more viscous formulations since they provide greater anaesthetic power and activity time when compared to formulations with equivalent amounts of anaesthetic agents in nanoparticles.

EXAMPLES

The following experimental examples illustrate the present invention, without, however, limiting its scope.

Example 1

Production of Anaesthetic Nanoparticles

Anaesthetic nanoparticles were prepared according to the composition of the phases presented on Table 1.

Firstly, the organic phase was prepared by dissolving the polymer (poly(ε-caprolactone), EUDRAGIT® S 100 (a copolymer of methacrylic acid and methyl methacrylate, with a ratio of the free carboxyl groups to the ester groups being approximately 1:2) or methyl polymethacrylate), the tensoactive (Span® 60F (sorbitan monostearate (pharmaceutical grade)) or Epikuron™ 170 (purified phospholipid)) and the mixture of active principles (lidocaine and prilocalne) in acetone. This phase was maintained under agitation and moderate heat (30 to 40° C.), until complete dissolution of the components. The aqueous phase was prepared in a separate beaker and consisted of the tensoactive (TWEEN® 80 (polysorbate 80)) dispersed in water. After complete dissolution of the components, the organic phase was slowly poured through a funnel over the aqueous phase, under moderate agitation at ambient temperature and then maintained under agitation for a further 10 minutes. This suspension was then concentrated in a rotary evaporator at a pressure of 3-6 bar and water bath temperature of 40-45° C., until attaining a final volume of approximately 100 mL.

TABLE 1

Composition of the phases, used for the production of nanoparticles

| Suspensions | LIDO (g) | PRL (g) | S100 (g) | PCL (g) | EPK (g) | SPA (g) | TWE (g) | $H_2O$ (mL) | ACE (mL) |
|---|---|---|---|---|---|---|---|---|---|
| 5-PCL-TWE | 2.5 | 2.5 |  | 1.0 |  |  | 1.0 | 320 | 480 |
| 5-EUD-TWE | 2.5 | 2.5 | 1.0 |  |  |  | 1.0 | (40%) | (60%) |
| 5-EUD-EPK | 2.5 | 2.5 | 1.0 |  | 0.7 |  | 0.7 |  |  |
| 3-PCL-TWE | 1.5 | 1.5 |  | 1.0 |  |  | 1.0 |  |  |
| 3-PCL-SPA | 1.5 | 1.5 |  | 1.0 |  | 0.7 | 0.7 |  |  |
| 3-EUD-TWE | 1.5 | 1.5 | 1.0 |  |  |  | 1.0 |  |  |
| 3-EUD-SPA | 1.5 | 1.5 | 1.0 |  |  | 0.7 | 0.7 |  |  |
| 3-EUD-EPK | 1.5 | 1.5 | 1.0 |  | 0.7 |  | 0.7 |  |  |

LIDO: lidocaine, PRL: prilocaine, S100: Eudragit S100 ®, PCL: Poly(ε)-caprolactone 65 Kd (Sigma Aldrich), EPK: Epikuron 170 ®; TWE: Tween 80 ®, SPA: Span 60 ®, $H_2O$: Water, ACE: Acetone.

The concentrated suspensions were assessed in relation to average diameter, total rate of lidocaine and prilocaine and association ratio of lidocaine and prilocaine to the nanocapsules (Table 2).

TABLE 2

Average diameter, association ratio and rates of active ingredients in the nanoparticles.

| Suspensions | Average diameter (nm) | Association ratio (%) | | Rate (%) | |
|---|---|---|---|---|---|
|  |  | Lidocaine | Prilocaine | Lidocaine | Prilocaine |
| 5-PCL-TWE | 132 | 86 | 78 | 96 | 98 |
| 5-EUD-TWE | 142 | 75 | 73 | 98 | 94 |
| 5-EUD-EPK | 181 | 87 | 86 | 103 | 98 |
| 3-PCL-TWE | 116 | 88 | 80 | 101 | 99 |
| 3-PCL-SPA | 164 | 91 | 79 | 89 | 93 |
| 3-EUD-TWE | 175 | 87 | 84 | 100 | 97 |
| 3-EUD-SPA | 198 | 83 | 81 | 86 | 90 |
| 3-EUD-EPK | 134 | 77 | 76 | 98 | 95 |

The assessment of diameter and rate of polydispersion of the particles in the suspension was determined by dynamic light scattering (Zetasizer® nano-ZS model ZEN 3600, Malvern, USA). The samples were diluted 500 times at ambient temperature in ultrafiltrated water.

In order to determine the total rate of lidocaine and prilocaine, the suspensions were treated with acetonitryl to dissolve all the components of the formulation. An aliquot of the suspension was then transferred to a 10 mL balloon flask and the volume was made up with acetonitryl. The solution was filtered through hydrophylic membrane (Millipore, 0.45

μm) and the lidocaine and prilocaine rates were then determined by high power liquid chromatography (HPLC).

The concentration of lidocaine/prilocaine incorporated to the nanostructures was determined by HPLC through the difference between the total concentrations of lidocaine/prilocaine in the formulations and the concentrations present in the aqueous phase of the suspension. The total concentrations associated to the nanostructures were determined by the dissolution of the nanocapsules in acetonitrile, as described above for determining the total rate of lidocaine and prilocaine. The concentrations of lidocaine/prilocaine present in the aqeous phase were determined by ultrafiltration-centrifugation of the suspensions (Ultrafree®-MC Millipore 10.000Å) during 5 minutes, at 12.000 rpm. In this manner the polymer nanoparticles and nanoemulsions were retained and the non-associated lidocaine/prilocaine passed through the membrane and was then quantified in the ultrafiltrate in the same conditions described above for determining the total concentration of local anaesthetics.

Furthermore, tests were performed in which different proportions/quantities of water and acetone were used (water: 533 mL/acetone: 267 mL; water: 300 mL/acetone: 300 mL; water: 400 mL/acetone: 400 mL); that confirmed that variations in the quantities and proportions of water and acetone, in the range tested, did not significantly influence the size of the nanoparticles or the rate of association of the anaesthetic agents to the nanoparticles.

Example 2

Preparation of the Hydrogels Containing the Suspensions of Nanocapsules and Nanoemulsions Hydrogels were prepared by incorporating Carbopol® 940 (carboxypolymethylene), to a final concentration of 0.25%, 0.75% and 1.5% to the nanoparticle suspensions prepared in accordance with Example 1 with the final masses being adjusted through the addition of distilled water so as to obtain a final nominal rate of 5% anaesthetics for formulations G 5-PCL-TWE, G 5-PCL-TWE 0.75% and G 5-EUD-EPK (prepared, respectively, from the concentrated suspensions 5-PCL-TWE and 5-EUD-EPK, produced in accordance to Example 1) and of 3% for formulation G 3-PCL-TWE (prepared from the concentrated suspension 3-PCL-TWE produced in accordance to Example 1).

The rheological features of the semi-solid formulations were assessed through the use of a Brookfield rotational viscometer, models RV DV I+ and LV DVII+PRO, with spindle SC4-25, at speeds of 2.0 and 2.5 RPM (Table 3).

TABLE 3

Viscosity of hydrogel gels containing carboxypolymethylene at concentrations of 0.25%, 0.75% and 1.5%

| % Carbopol 940 | Formulation | Viscosity (cP) Velocity 2.0 RPM | Velocity 2.5 RPM |
|---|---|---|---|
| 1.5 | G 5-PCL-TWE | 791000 | 659400 |
|  | G 3-PCL-TWE | 730000 | 604100 |
|  | G 5-EUD-EPK | 307200 | 251900 |
| 0.75 | G 5-PCL-TWE 0.75% | 640000 | 520200 |
|  | G 3-PCL-TWE 0.75% | 366000 | 315400 |
|  | G 5-EUD-EPK 0.75% | 102000 | 75400 |
| 0.25 | G 5-PCL-TWE 0.25% | 215000 | 178000 |
|  | G 3-PCL-TWE 0.25% | 115000 | 104000 |

Example 3

Assessment of Anaesthetic Activity In Vivo

The in vivo percentage rate of anaesthesia promoted by hydrogels containing nanoparticles of lidocaine and prilocaine was determined in mice using the "Tail Flick" technique (Kolesnikov Y. e col. "Evaluation of the tail formalin test in mice as a new model to assess local analgesic effects". *Brain Research*, v. 1029, p. 217-223, 2004) and, for comparison, the commercially available product EMLA® (a cream containing 2.5% lidocaine and 2.5% prilocaine produced by AstraZeneca do Brasil Ltda.).

The anaesthetic effect was analysed using 5 distinct groups:

Positive control group (1 group): Topical application of commercial product EMLA®.

Negative control group (1 group): Hydrogel containing nanocapsule without pharmacons.

Test groups (4 groups): Topical application of hydrogels with nanoparticles containing lidocaine and prilocaine, complying with the anaesthetic rates and nanoparticle compositions defined on Table 4.

TABLE 4

Anaesthetic rates and nanoparticle compositions used in the tests for anaesthetic effect

| Gel | Nanoparticle composition | Lidocaine rate in gel % | Prilocaine rate in gel % | Carbopol rate in gel % |
|---|---|---|---|---|
| G5-PCL-TWE | 5-PCL-TWE | 2.55 | 2.5 | 1.5 |
| G5-EUD-EPK | 5-EUD-EPK | 2.45 | 2.38 | 1.5 |
| G3-PCL-TWE | 3-PCL-TWE | 1.55 | 1.47 | 1.5 |
| G5-PCL-TWE 0.75 | 5-PCL-TWE | 2.55 | 2.5 | 0.75 |

The tests were performed with adult, female, albino Swiss mice weighing between 30 and 35 g. The animals were maintained in the Biotherium in cages containing not more than 5 mice with free access to water and food.

The animals were maintained in restrainers that allowed access to their extended tails during the experiment. Firstly, base line sensitivity was ascertained (BL) for each animal using an analgesia meter (Tail Flick Analgesia Meter, model EFF-300). Initially, the tails of the animals were immerged in DMSO for 2 minutes. The DMSO was then removed with damp sterile gauze following which the tails were carefully immersed in Eppendorf type tubes containing the semi-solid formulation to be tested according to the group. After 10 and 20 minutes application of the intended formulation, it was removed using damp sterile gauze. The animal's tail was then placed on the surface of the equipment equipped with a heated metal filament. Analgesia is assessed measuring latency time (TL) for the tail movement in reaction to the heat induced stimulus. The maximum exposure time to the radiation was pf 6 seconds to minimise tissue lesions to the animal's tail. Three latency time measurements were taken for each animal.

The results were assessed in relation to the percentage of anaesthesia achieved for each animal according to the following equation:

$$\% \text{ anaesthesia} = 100 \times (TL - BL)/(6 - BL)$$

wherein: TL=Latency Time under effect of the anaesthetic formulation; TB=Basal Latency Time; 6=Maximum time of exposure to the radiation.

The statistical analysis of the assessment tests for anaesthetic activity was performed in accordance with the ANOVA method (Sigma-Stat®, Jandel Scientific, USA), using the commercial cream EMLA as reference.

The results obtained confirmed that topical administration of hydrogels G5-PCL-TWE, 5-EUD-EPK, 3-PCL-TWE and G5-PCL-TWE 0.75% through an exposure time of 20 minutes before removal of the formulation promoted a considerable increase in the anaesthetic effect percentage and duration when compared to the commercially available EMLA® cream and, furthermore, also demonstrated that even the hydrogel 3-PCL-TWE containing only 3% of anaesthetics presented greater anaesthetic effect than that verified in the commercially available EMLA® cream that contains 5% anaesthetics (FIG. 1).

Figure 2:
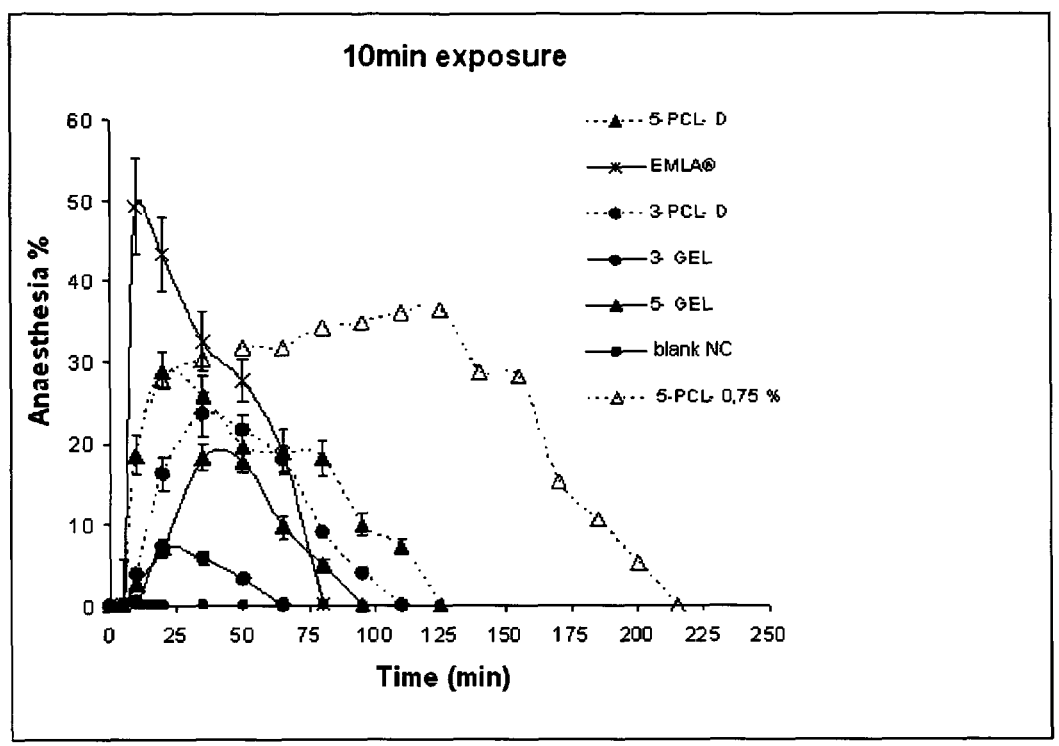
FIG. 2: percentage of anaesthesia promoted by the hydrogels G5-PCL-TWE, G5-EUD-EPK, G3-PCL-TWE, G5-PCL-TWE 0.75% and the commercially available EMLA® cream 10 minutes after topical administration to the tails of rats (n=11/group).

Furthermore, it was also possible to verify that the topical administration of hydrogels G5-PCL-TWE, 5-EUD-EPK, 3-PCL-TWE and G5-PCL-TWE 0.75% through an exposure time of 10 minutes before removal of the formulation provided an anaesthesia profile similar to that seen in the test with an exposure time of 20 minutes but that this was not the case of the commercial cream EMLA® that promoted far less intense anaesthesia after the 20 minute exposure than with the 10 minute exposure (FIG. 2).

All the publications mentioned in the above descriptive report are incorporated herein as reference. Various modifications and variations to the above description of the invention shall become evident to those versed in the techniques, without departing from the scope or spirit of the invention.

The invention claimed is:

1. An anaesthetic composition for topical application to the skin or mucosa, comprising:
   (i) a suspension of polymeric nanocapsules consisting of:
      (a) poly (ε-caprolactone);
      (b) a combination of lidocaine and prilocalne;
      (c) a tensoactive agent selected from the group consisting of sorbitan monostearate, purified phospholipid, polysorbate 80, or mixtures of these materials; and
      (d) water;
   (ii) at least one carboxypolymethylene as a viscosity enhancer,
   wherein said polymeric nanocapsules have an average particle diameter between 116 nm and 164 nm.

2. The anaesthetic composition according to claim 1, wherein said composition comprises a concentration of 0.5 to 10% of lidocaine and 0.5 to 10% of prilocalne.

3. The anaesthetic composition according to claim 2, wherein said composition comprises concentrations of 2.5% of lidocaine and 2.5% of prilocalne.

4. The anaesthetic composition according to claim 1, wherein the polymeric nanocapsules are produced by the interface deposit of pre-formed polymers.

* * * * *